United States Patent [19]

Harsányi et al.

[11] Patent Number: 5,292,933
[45] Date of Patent: Mar. 8, 1994

[54] PROCESS FOR THE RESOLUTION OF THREO-3-[(2-AMINOPHENYL)-THIO]-2-HYDROXY-3-(4-METHOXY-PHENYL)PROPIONIC ACID

[75] Inventors: Kálmán Harsányi; Elemér Fogassy; Mária Ács; Tibor Gizur; Zsuzsanna Aracs née Tischler; Katalin Berki; László Tőke; Zsuzsanna Mártonffy née Jászay, all of Budapest, Hungary

[73] Assignee: Richter Gedeon Vegyeszeti Gyar RT, Budapest, Hungary

[21] Appl. No.: 684,892

[22] PCT Filed: Jun. 29, 1990

[86] PCT No.: PCT/HU90/00045

§ 371 Date: Apr. 9, 1991

§ 102(e) Date: Apr. 9, 1991

[87] PCT Pub. No.: WO91/00270

PCT Pub. Date: Jan. 10, 1991

[30] Foreign Application Priority Data

Jun. 30, 1989 [HU] Hungary ............................. 3335/89
Jun. 30, 1989 [HU] Hungary ............................. 3336/89

[51] Int. Cl.$^5$ ................................................ C07B 57/00
[52] U.S. Cl. ........................................ 562/401; 564/304; 562/430
[58] Field of Search ......................... 564/304; 562/401

[56] References Cited

U.S. PATENT DOCUMENTS

| | | | |
|---|---|---|---|
| 4,036,852 | 7/1977 | Boesten | 548/531 |
| 4,416,819 | 11/1983 | Nagao et al. | 544/491 |
| 4,533,748 | 8/1985 | Manghisi et al. | 562/401 |
| 4,931,587 | 6/1990 | Piselli | 562/401 |
| 5,008,433 | 4/1991 | Palmer | 560/17 |

*Primary Examiner*—Jose' G. Dees
*Assistant Examiner*—Vera C. Clarke
*Attorney, Agent, or Firm*—Herbert Dubno; Jonathan Myers

[57] ABSTRACT

The invention relates to a novel process for the resolution of an acid mixture (hereinafter: threo acid mixture) containing (+)-threo-3-[(2-aminophenyl)thio]-2-hydroxy-3-(4-methoxyphenyl)-propionic acid [hereinafter: (+)-threo acid] and (−)-threo-3-[(2-aminophenyl)-thio]-2-hydroxy-3-(4-methoxyphenyl)-propionic acid [hereinafter: (−)-threo acid].

3 Claims, No Drawings

PROCESS FOR THE RESOLUTION OF THREO-3-[(2-AMINOPHENYL)-THIO]-2-HYDROXY-3-(4-METHOXY-PHENYL)PROPIONIC ACID

FIELD OF THE INVENTION

This invention relates to a novel process for the resolution of an acid mixture (hereinafter: threo acid mixture) containing (+)-threo-3-[(2-aminophenyl)thio]-2-hydroxy-3-(4-methoxyphenyl)propionic acid [hereinafter: (+)-threo acid] and (−)-threo-3-[(2-aminophenyl)-thio]-2-hydroxy-3-(4-methoxyphenyl)propionic acid [hereinafter: (−)-threo acid].

BACKGROUND OF THE INVENTION

The (+)-threo acid is an important raw material of the therapeutically active (2S,3S)-3-acetoxy-5-dimethylaminoethyl-2-(4-methoxyphenyl)-2,3-dihydro-1,5-benzothiazepin-4(5H)-one hydrochloride (generic name: diltiazem), a known antianginal drug acting as a calcium antagonist.

There are several processes known from the literature for the preparation of the (+)-threo acid.

A resolution process using L-lysine as resolving agent is described in the published German patent application (DE-OS) No. 3,337,176. However, the particularly costly L-lysine is used in a 4-fold excess and,; in addition, it is difficult and expensive to recover L-lysine in its acid form from the mother liquors.

According to another method [Helv. Chim. Acta 67, 916 (1984)], the racemic threo acid is resolved by using cinchonidine in ethanol. This method is characterized by the use of an extraordinarily high amount of alcohol as solvent and by a 48-hour time demand of crystallization.

According to the method described in the U.S. Pat. No. 4,416,819, an equivalent amount of (+)-α-phenylethylamine each is employed for both forms of the racemic acid in order to resolve the racemic threo acid in water. In our own examinations, a (+)-threo acid with an optical purity of only 87%, $[\alpha]_D^{20} = +302°$ (c=0.3, ethanol), was obtained in a yield of 79% when the resolution and subsequent crystallization of the diastereomeric salt were carried out by using the method cited above.

In the process described in the Hungarian patent specification No. 193,230, the acid addition salt of 0.5 to 0.6 molar equivalent of (+)-α-phenylethylamine is used as resolving agent; a method, useful to enrich the valuable (+)-threo acid in the remaining threo acid mixture is also described in the above specification.

OBJECT OF THE INVENTION

It is the object of the present invention, to provide a process by providing the (+)-threo acid economically, in a high optical purity and good yield by using simple technological steps and to provide as well an inexpensive and easily available resolving agent.

DESCRIPTION OF THE INVENTION

The invention is based on the recognition that D-(−)-phenylglycine amide [hereinafter: (−)-PGA] and L-(+)-phenylglycine amide [hereinafter: (+)-PGA], respectively form a slightly (less) soluble diastereomeric salt with the (−)-threo or (+)-threo acid, respectively.

Thus, the present invention essentially relates to a novel process for the resolution of an acid mixture ("threo acid mixture") containing (+)-threo-3-[(2-aminophenyl)thio]-2-hydroxy-3-(4-methoxyphenyl)-propionic acid ["(+)-threo acid"] and (−)-threo-3-[2-aminophenyl)thio]-2-hydroxy-3-(4-methoxyphenyl)-propionic acid ["(−)-threo acid"], which comprises using D-(−)-phenylglycine amide or L-(+)-phenylglycine amide, respectively as resolving agent.

Although (+)-PGA and (−)-PGA used for separating the threo acid mixture can be prepared in any optional way (see e.g. the German patent specification (DE-PS) No. 2,547,548), a particularly economical process for the preparation of the above resolving agents is also part of the present invention namely, racemic or nearly racemic α-phenylglycine amide (hereinafter: PGA mixture) can be separated to its enantiomers in a good, yield and satisfying purity by using (−)-threo acid which has been considered as a side product of no use up to the present. The racemic or nearly racemic threo acid mixture can be resolved to its enantiomers in a suitable quality by using the aqueous solutions containing (+)-PGA or (−)-PGA, respectively obtained according to the process of the present invention.

Thus, by using this most preferred variation (embodiment) of the present invention, the preparation of (+)-threo acid can be realized in a very economical way without any demand on an expensive, optically active resolving agent. The resolving agent required to prepare (+)-threo acid can be obtained by utilizing (−)-threo acid, which is accumulated in large amount or is continuously formed, in the preparation of the (+)-threo acid.

It should be noted that (+)-PGA also forms a slightly water-soluble diastereomeric salt with (+)-threo acid, however, this resolution process bears no economical importance.

It should also be remarked that the process of the present invention is not aimed to obtain solid (+)-PGA and (−)-PGA from the aqueous solutions containing (+)-PGA or (−)-PGA, respectively, since the (+)-threo acid can be resolved in an aqueous medium, also and on the other hand, PGA is partially decomposed under heat effects accompanying its recovery.

Racemic or nearly racemic α-phenylglycine amide used as starting substance can be prepared according to e.g. J. Am. Chem. Soc. 71, 78 (1949).

The resolution of the threo acid mixture can be achieved by using any method commonly used for resolution. It has been found to be preferred first to dissolve the threo acid mixture in water by the means of sodium hydroxide solution at 50° to 80° C., then to pour to the mixture ethanol in an amount being nearly equal to that of the water used, thereafter to add portionwise the corresponding (−)- or (+)-PGA hydrohalide, respectively, preferably hydrochloride in a solid or dissolved form in an excess of 5 to 15% calculated for the enantiomer to be separated. The precipitated diastereomeric salt is filtered, dissolved in an 8 to 12-fold amount of water and decomposed by adding aqueous hydrochloric acid (pH=2 to 4). The corresponding (+)- or (−)-threo acid, respectively is obtained as a precipitate.

The mother liquor remaining after separation of the diastereomeric salt is acidified (ph=2 to 4) by aqueous hydrochloric acid and the solution is stirred under cooling by ice-water. The precipitate (i.e. the oppositely rotating enantiomer of the threo acid obtained by decomposing the salt) is filtered.

The remaining mother liquor contains the starting resolving agent thus, it can be used in further resolution steps or cycles.

The PGA mixture can be resolved by using any method commonly employed in resolution processes. According to a process found to be most advantageous in our investigations, an acid addition salt, preferably hydrochloride of the starting α-phenylglycine amide is dissolved in water at 50° to 80° C. and an aqueous solution of (−)-threo acid prepared with an alkaline metal hydroxide, preferably sodium hydroxide and maintained at 50° to 80° C. is portionwise added (if necessary, the pH value of both solutions is previously adjusted to 7). The solution obtained is allowed to cool to 20°-30° C. and then further cooled by ice-water. The precipitate is filtered.

The filtrate is an aqueous solution containing (+)-PGA, which can directly be used as a resolving agent.

The precipitate filtered out is (−)-threo acid, which may be repeatedly be used for separation.

SPECIFIC EXAMPLES

The process of the invention is illustrated in detail by the following non-limiting Examples.

EXAMPLE 1

Preparation of an aqueous solution containing (+)-α-phenylglycine amide

A solution prepared from 3.6 g (0.113 mole) of (−)-threo acid with 22 ml of 0.5N sodium hydroxide and 22 ml of water, clarified by activated carbon and heated to 70° C. is portionwise added to a solution of 3.7 g (0.0198 mole) of α-phenylglycine amide hydrochloride prepared in 40 ml of water at 70° C. (If necessary, the pH value of both above solutions is adjusted to 6.5-7.5 by adding hydrochloric acid or sodium hydroxide solution, respectively before combining them.) The solution cooled down to room temperature is cooled by ice-water for an additional 30 minutes. During crystallization the pH value is several times controlled and maintained between 6.5 and 7.5; when necessary, the pH value is appropriately adjusted as described above.

The precipitate is filtered to obtain 5.0 g of diastereomeric salt containing (−)-PGA-(−)-threo acid as the main bulk, $[\alpha]_D^{20}=-215°$ (c=0.3, water).

The filtrate contains 1.37 g (0.0091 mole) of (+)-PGA, $[\alpha]_D^{20}=+92°$.

EXAMPLE 2

Preparation of an aqueous solution containing (−)-α-phenylglycine amide 5.0 g of the diastereomeric salt filtered out as described in the preceeding Example is decomposed in 100 ml of water at 70° C. in such a way that the solution is heated to the boiling point while adjusting the pH value of the solution to 3 by adding 1N hydrochloric acid. The mixture is cooled and allowed to stand at room temperature, then cooled by ice-water for 1 hour and the precipitate is filtered to give 3.4 g of (−)-threo acid, $[\alpha]_D^{20}=-335°$ (c=0.3, ethanol).

The filtrate contains 1.48 g (0.0099 mole) of (−)-PGA hydrochloride.

The $[\alpha]_D^{20}$ value of the filtrate is −82°.

EXAMPLE 3

Preparation of (−)-threo-3-[(2-aminophenyl)thio]-2-hydroxy-3-(4-methoxyphenyl)propionic acid [(−)-threo acid]

40 ml of ethanol and a solution of 1.0 g (0.0054 mole) of (−)-PGA hydrochloride ($[\alpha]_D^{20}=-92°$ (1N HCl)) in 10 ml of water are portionwise added to the solution containing 3.2 g (0.01 mole) of racemic threo acid in a mixture of 30 ml of water and 5 ml of 1N sodium hydroxide solution at 70° C. If necessary, the pH value of the solution obtained is adjusted to 7 after combining. The solution is allowed to cool while stirring. From the beginning of crystallization, a cooling by ice-water is employed for 30 minutes. The precipitate is filtered and the filtrate is set aside for further working up (processing). In this way 2.4 g of (−)-PGA-(−)-threo acid diastereomeric salt are obtained, $[\alpha]_D^{20}=-218.7°$ (c=0.3, water). After recrystallization of this diastereomeric salt from 85 ml of water, 2.1 g of product are obtained, $[\alpha]_D^{20}=-16°$ (c=0.3, ethanol).

The diastereomeric salt obtained as described above is dissolved in 50 ml water at 70° C. while adjusting the pH value of the solution to 3 by 1N hydrochloric acid. After letting the mixture stand for 1 hour, the mixture is cooled by ice-water for 30 minutes, then the precipitate is filtered to give 1.1 g (68.8%) of the title compound, m.p.: 136°-138° C., $[\alpha]_D^{20}=-330.5°$ (c=0.3, ethanol).

From the mother liquor set aside after separation of the diastereomeric salt, (+)-threo-3-[(2-aminophenyl)-thio]-2-hydroxy-3-(4-methoxyphenyl)propionic acid [(+)-threo acid] is obtained as follows.

After adjusting the pH value of the remaining mother liquor to 3 by 1N hydrochloric acid, the mixture is crystallized first at room temperature for 1 hour, then under cooling by ice-water for 30 minutes. After filtering the precipitate, 1.5 g (93.8%) of (+)-threo acid are obtained, $[\alpha]_D^{20}=260.6°$ (c=0.3, ethanol).

EXAMPLE 4

Preparation of (+)-threo-3-[(2-aminophenyl)thio]-2-hydroxy-3-(4-methoxyphenyl)propionic acid [(+)-threo acid]

6.4 g (0.02 mole) of racemic threo acid are dissolved in a mixture of 17 ml of water and 43 ml of 0.5N sodium hydroxide solution at 70° C. and then 80 ml of methanol and 2.0 g (0.011 mole) of (+)-PGA $[\alpha]_D^{20}=-92°$ (1N HCl) dissolved in 20 ml of water are portionwise added. If necessary, the pH value of the solution is adjusted to 7 after combination. The solution is allowed to cool down while stirring. The mixture is permitted to stand for 1 hour from the beginning of crystallization, then it is cooled by ice-water for 30 minutes, thereafter the precipitate is filtered to obtain 3.5 g of product [(+)-PGA-(+)-threo acid diastereomeric salt].

The diastereomeric salt obtained as described above is dissolved in 70 ml of water by heating the solution to its boiling point and adjusting its pH value to 3 by 1N hydrochloric acid. Subsequently, the mixture is cooled by ice-water for 1 hour, then the precipitate is filtered and the filtrate is set aside for further working up (processing). In this way 2.1 g (65.6%) of the title compound are obtained, m.p.: 138°-139° C., $[\alpha]_D^{20}=+346°$ (c=0.3, ethanol).

The mother liquor set aside after decomposing the diastereomeric salt can be used in a further resolution step as follows.

3.2 g (0.01 mole) of racemic threo acid are dissolved at 80° C. in a mixture containing 30 ml of water and 21.5 ml of 0.5N sodium hydroxide solution. To this solution, the mother liquor set aside after decomposing the diastereomeric salt is added, the pH value of which has previously been adjusted to 7 by 1N sodium hydroxide solution. If necessary, the pH value of the solution obtained is adjusted to 7 after combination. This solution is allowed to cool down under stirring. After beginning of crystallization, cooling by ice-water is used for 30 minutes, then the precipitate is filtered to give 2.0 g of product [(+)-PGA-(+)-threo acid diastereomeric salt].

The diastereomeric salt obtained as described above is dissolved in 30 ml of water by heating the solution to its boiling point while adjusting its pH value to 3 by 1N hydrochloric acid. Thereafter, the mixture is cooled at room temperature for 1 hour, then by ice-water for 30 minutes and the precipitate is filtered to yield 1.3 g (81%) of the title compound, m.p.: 134°–136° C., $[\alpha]_D^{20} = +327°$ (c=0.3, ethanol).

We claim:

1. Process for the resolution of a threo-acid mixture containing (+)-threo-3-[(2-aminophenyl)thio]-2-hydroxy-3-(4-methoxyphenyl)-propionic acid and (−)-threo-3-[(2-aminophenyl)thio]-2-hydroxy-3-(4-methoxy-phenyl)-propionic acid, which comprises a)
  (i) preparing a solution containing D-(−)-phenylglycine amide from a mixture containing same and L-(+)-phenylglycine amide by the use of (−)-threo-3-[(2-aminophenyl)thio]-2-hydroxy-3-(4-methoxyphenyl)-propionic acid as resolving agent and using the solution obtained as a resolving agent for the resolution of the threo acid mixture; or
  (ii) using an acid addition salt of D-(−)-phenylglycine amide in a solid or dissolved form as a resolving agent,
  to obtain (−)-threo-3-[(2-aminophenyl)thio]-2-hydroxy-3-(4-methoxyphenyl)-propionic acid; or b)
  (i) preparing a solution containing L-(+)-phenylglycine amide from a mixture containing L-(+)-phenylglycine amide and D-(−)-phenylglycine amide by the means of (+)-threo-3-[(2-aminophenyl)thio]-2-hydroxy-3-(4-methoxyphenyl)-propionic acid as resolving agent and using the solution obtained as a resolving agent for the resolution of the threo acid mixture; or
  (ii) using an acid addition salt of L-(+)-phenylglycine amide in a solid or dissolved form as a resolving agent to obtain (+)-threo-3-[(2-aminophenyl)thio]-2-hydroxy-3-4(4-methoxyphenyl)-propionic acid.

2. A process as claimed in claim 1, which comprises using the acid addition salt of D-(−)-phenylglycine amide or the acid addition salt of L-(+)-phenylglycine amide, respectively in a 1.0 to 1.5 molar equivalent excess calculated for the corresponding (−)- or (+)-threo acid, respectively.

3. A process as claimed in claim 2, which comprises using a hydrohalide salt, as acid addition salt.

* * * * *